United States Patent [19]

Rodero

[11] Patent Number: 4,822,613

[45] Date of Patent: Apr. 18, 1989

[54] WATER-SOLUBLE FOAMABLE INSECTICIDALLY-ACTIVE COMPOSITIONS

[75] Inventor: Alejandro Rodero, Racine, Wis.

[73] Assignee: S. C. Johnson & Son, Inc., Racine, Wis.

[21] Appl. No.: 941,326

[22] Filed: Dec. 15, 1986

[51] Int. Cl.$^4$ ............................................. A01N 25/00
[52] U.S. Cl. ...................................... 424/405; 424/409
[58] Field of Search ....................... 424/405, 409, 411; 521/99

[56] References Cited

U.S. PATENT DOCUMENTS

| | | | |
|---|---|---|---|
| 3,524,911 | 8/1970 | Leavitt | 421/45 |
| 3,816,610 | 1/1972 | Lusby | 424/419 |
| 3,970,584 | 7/1976 | Hart et al. | 252/305 |
| 4,339,550 | 7/1982 | Palenczar et al. | 521/107 |
| 4,563,344 | 1/1986 | Kotz et al. | 424/405 |
| 4,663,341 | 5/1987 | Jacobson | 514/403 |

FOREIGN PATENT DOCUMENTS 1107140 3/1968 United Kingdom .

*Primary Examiner*—Thuman K. Page
*Assistant Examiner*—L. R. Horne

[57] ABSTRACT

A water-soluble, foamable, insecticidally-active composition is disclosed. Also disclosed are methods for producing such a composition. The water-soluble, foamable, insecticidally-active composition comprises an aqueous phase, an insecticidally-active toxicant, and a foam-causing ingredient. The aqueous phase comprises water. The foam-causing ingredient must be capable of dispersing the insecticidally-active toxicant throughout the aqueous phase, to produce a toxicant-in-water dispersion. The foam-causing ingredient is present in an amount effective to enable the toxicant-in-water dispersion to form-in-place a water-soluble and insecticidally-active foam. The water-soluble aspect of the foam allows dissolving the foam (utilizing sufficient water) when desired.

8 Claims, No Drawings

WATER-SOLUBLE FOAMABLE INSECTICIDALLY-ACTIVE COMPOSITIONS

FIELD OF THE INVENTION

This invention is directed to water-soluble, foamable, insecticidally-active compositions, and to methods for producing such water-soluble, foamable, insecticidally-active compositions.

BACKGROUND OF THE INVENTION

Aerosol insecticidal compositions are well known. For example, U.S. Pat. No. 3,524,911 (to Leavitt) teaches such compositions. The Leavitt compositions are said to form a self-sustaining, relatively rigid insecticide-containing foam which, the patent discloses, is able to persist for prolonged periods of time. The aerosol-spray compositions disclosed in the Leavitt patent, which compositions are characterized as comprising an essentially nonaqueous mixture, are insoluble in water.

The insecticidal compositions disclosed herein, in contradistinction to the insecticidal compositions disclosed in the Leavitt patent, are water soluble.

British Pat. No. 1,107,140 (to Mitchell et al.) discloses an aerosol-dispensed, insecticide composition which is applied as a spray, not a foam. This British patent, in fact, teaches away from the production of a foam. More particularly, Mitchell et al. teaches producing a mist which is designed to remain air-borne for a desired period of time. (One such air-borne type insecticide is referred to in the art as a "flying insect killer" or FIK type insecticide.) Whereas the instant invention is specifically designed and adapted to be applied onto a surface, and into cavities, crevices and the like.

In the area of insect control, it is desirable to be able to present a positive barrier to insects, such a barrier being generally not providable by an air spray-type of application.

In the related area of rodent control, U.S. Pat. No. 3,816,610 (to Lusby) discloses a palatable rodent-control material that can be formed-in-place and used, for example, to fill holes through which the rodents are accustomed to run. The foam, disclosed in the Lusby patent, is said to be able to expand in volume to fill up a cavity, taking the shape thereof and thereafter becoming rigid. The plastic foam cellular structures disclosed in the Lusby patent, while useful for one purpose, because they become rigid and are insoluble in water, unfortunately cannot readily be removed from many cavities into which they are formed-in-place.

Yet, in the area of insect control it is desirable not only to prevent a positive insect barrier in, for example, cracks and crevices, beneath doors and around windows, and in drain pipes from fixtures such as sinks and tubs, it is also desirable to present such a positive insect barrier that is readily removable, when desired.

Also related to the area of insect control is U.S. Pat. No. 3,970,584 (to Hart et al.), which discloses, in addition to a variety of foam compositions, a foam-forming insect repellent composition. More particularly, the insect repellent compositions disclosed in the Hart et al. patent are referred to in the art as "personal care" products (i.e., lotions, skin creams and the like) which, upon application, generally either form thin films on or are absorbed into the skin. Whereas the present invention is directed to a positive insect barrier.

While insect repellents function by repelling insects away from a situs, many insecticidally-active substances function by drawing insects toward a situs for the purpose of causing death upon contact with an insect toxicant-containing substance.

Another notable difference between the present invention and the Hart et al. patent is that the Hart et al. patent teaches that its insect-repellent composition requires a complex propellant system consisting essentially of nitrous oxide and isobutane, which propellant system, the Hart et al. patent teaches, must be present in specified quantities, to achieve the stated objects of the Hart et al. patent. In contradistinction, the present invention has no such complex propellant-system requirement, and any suitable propellant can be utilized.

Accordingly, a foamable, insecticidally-active composition, not dependent upon a complex propellant system to produce a foam, wherein the foam is able to expand to substantially fill a cavity, and wherein the foam is water-soluble so as to be readily removable (from the cavity) when desired, is presently in demand and of commercial significance.

The instant invention is thus distinguishable from prior art discussed above in that the foamable water-soluble insecticidally-active composition disclosed herein is able to produce an expandable foam capable not only of substantially filling a cavity (in place) but also of existing in a stable form in the cavity for hours or weeks (depending upon, inter alia, water content of the composition, the amount and type of surfactant or foaming agent in the composition, and the quantity and type of propellant that is utilized).

SUMMARY OF THE INVENTION

The present invention is directed to a water-soluble, foamable, insecticidally-active composition, and to methods for producing such a water-soluble, foamable, insecticidally-active composition. The water-soluble, foamable, insecticidally-active composition, which is characterized as an oil-in-water emulsion, comprises an aqueous phase, an insecticidally-active toxicant, and a foam-causing ingredient or surfactant.

The water-soluble, foamable, insecticidally-active composition may further preferably include a foam stabilizer (an optional ingredient) if desired.

Still further, yet other optional ingredients, such as an antifoaming agent, can be included (if desired), in accordance with the principles of the present invention.

The aqueous phase comprises water. A suitable insecticidally-active toxicant must be capable of being dispersed throughout the aqueous phase. A suitable foam-causing ingredient or surfactant must be capable of dispersing the insecticidally-active toxidant throughout the aqueous phase, to produce a toxidant-in-water dispersion. The foam-causing ingredient or surfactant, moreover, must be present in an amount effective to enable the toxicant-in-water dispersion to form a water-soluble and insecticidally-active foam.

Depending upon a number of factors, e.g. the amount of water present in the insecticide composition, the amount and type of foam-causing ingredient or surfactant present in the composition, and the quantity and/or type of propellant that is utilized, the foam can be formulated so as to be substantially stable for hours or weeks, as desired.

The optional foam stabilizer ingredient (mentioned above), if present, is preferably present in an amount effective to further stabilize the water-soluble and insecticidally-active foam.

Illustrative methods of producing the insecticidally-active composition of the present invention are presented below.

DETAILED DESCRIPTION OF PREFERRED EMBODIMENTS

While the present invention is susceptible to embodiment in various forms, a number of water-soluble, foamable and insecticidally-active compositions and methods of producing such compositions, embodying the principles of the present invention, are hereinafter described in detail. The present disclosure, therefore, is to be considered an exemplification of the present invention, without limitation to the specific embodiments discussed.

As briefly mentioned above, the water-soluble, foamable and insecticidally-active composition of the present invention comprises an aqueous phase, an insecticidally-active toxicant, and a foam-causing ingredient or surfactant. A foam stabilizer may optionally be included.

The aqueous phase is present in the foamable composition in an amount of about 40 to about 98 wt.-%, preferably about 65 to about 98 wt.-%, and more preferably about 75 to about 98 wt.-%, based upon the weight of the foamable composition.

The insecticidally-active toxicant is present in the foamable composition in an amount of about 0.001 to about 5 wt.%, preferably about 0.01 to about 2 wt.-%, and more preferably about 0.1 to about 1 wt.-% based upon the weight of the foamable composition.

The foam-causing ingredient is present in the foamable composition in an amount of about 0.2 to about 40 wt.-%, preferably about 0.5 to about 10 wt.-%, and more preferably about 1 to about 5 wt.-%, based upon the weight of the foamable composition.

When the foamable composition further includes the optional foam stabilizer ingredient, the foam stabilizer is present in the foamable composition in an amount of about 0.1 to about 20 wt.-%, preferably about 0.1 to about 5 wt.-%, and more preferably about 0.1 to about 2 wt.-%, based upon the weight of the foamable composition.

The water-soluble, foamable, insecticide composition of the present invention has many of the characteristics of a "water-out" emulsion. That is, the present insecticidally-active composition has many of the characteristics of an oil-in-water emulsion.

The aqueous phase comprises water. A suitable insecticidally-active toxicant must be capable of being dispersed throughout the aqueous phase. A suitable foam-causing ingredient or surfactant must be capable of dispersing the insectically-active toxicant throughout the aqueous phase to produce a toxicant-in-water dispersion. The foam-causing ingredient or surfactant, moreover, must be present in an amount effective to enable the toxicant-in-water dispersion to form a water-soluble and insecticidally-active foam. The resultant foam is specifically adapted to be able to expand (in place) in a manner so as to substantially fill a cavity, thereby presenting a positive insect barrier.

Depending upon a variety of factors including, but not limited to, the amount of water that is present in the foamable insecticide composition, the amount and/or type of surfactant or foam-causing ingredient that is present in the composition, and the quantity and/or type of propellant that is utilized, moreover, the resultant foam may be stable for hours or weeks.

The optional foam stabilizer ingredient (mentioned above), if present, is preferably present in an amount effective to further stabilize the foam. Furthermore, the water-soluble aspect or feature of this cavity-filling foam renders the foam readily removable from the cavity when it is desirable to do so.

For example, the water-soluble foam is adapted, as mentioned above, to be applied into a cavity of void space (such as a pipe drain line) and is further adapted to substantially fill up such a void space, thereby providing a positive insect barrier. The void-filling water-soluble foam, in turn, presents a sufficiently insecticidally-active exterior surface so that "insect-kill" takes place in a relatively short period of time (i.e., within about 1 hour, and even less) when an insect comes into contact with such a surface. Moreover, the water-soluble aspect of the formed-in-place foam enables an individual, who is able to direct a sufficient amount of water onto the foam, to dissolve the foam thereby unblocking the void space when it is desirable to do so.

Still further, the water-soluble, foamable and insecticidally-active composition can be dispensed from various types of dispensing systems and equipment, e.g., from spray guns, portable aerosol cans, etc., to provide an advantageous way of applying the instant water-soluble, foamable and insecticidally-active composition into a variety of void spaces including, but not limited to, cracks and crevices, beneath doors and around windows, in pipe or other conduit. (The present foam can conveniently be formed-in-place in a relatively dry area or even on top of standing water.) Because the formed-in-place foam expands significantly, once in the void space, the formed-in-place foam substantially fills the void space, thereby providing the positive insect barrier mentioned above.

The water-soluble, foamable and insecticidally-active composition further preferably comprises an effective amount of a propellant, for causing the surfactant-containing toxicant-in-water dispersion to produce the water-soluble and insecticidally-active foam.

When the foamable composition further includes the optional propellant ingredient, the propellant is present in the foamable composition in an amount of about 1 to about 50 wt.-%, preferably about 1 to about 25 wt.-%, and more preferably about 5 to about 20 wt.-%, based upon the weight of the foamable composition.

Normally, the selected propellant is immiscible with the aqueous phase; but it need not be. In particular, selected water-soluble propellants, such as dimethyl ether (DME), are suitable for purposes of the present invention. Further suitable water-soluble or partially water-soluble propellants include nitrous oxide (which is relatively soluble in water) and carbon dioxide (which is partially soluble in water).

A number of the desired characteristics of the formed-in-place foam, such as extent or degree of expansion, durability, relative dryness or wetness, etc., can selectably be controlled, moreover, by altering the amount of propellant and/or foam-causing ingredient that is present in the foamable composition. To this end, the amount of propellant, based upon the weight of the propellant in relation to the total weight of the foamable, insecticidally-active composition together with the weight of the propellant, can suitably range from about 5 to about 40 wt.-%, based upon the total weight of the insecticidally-active composition-and-propellant mixture.

Suitable propellants, for these purposes include, but are not limited to, liquified and compressed gases. Suitable liquified gases include hydrocarbon propellants (such as $C_1$ to $C_4$ hydrocarbons), halogenated propellants (such as the various commercially-available halogenated propellants known in the art as "Freon"), and DME. Illustrative of the preferred hydrocarbon propellants are propane, n-butane, isobutane, and mixtures thereof. Suitable compressed gases include air, nitrogen, nitrous oxide, and carbon dioxide.

A presently preferred propellant, known in the art as "A-46", has a vapor pressure of about 46 pounds per square inch gauge (psig) and comprises about 80 mole percent isobutane and about 20 mole percent propane.

The foam-causing ingredient or surfactant may suitably be selected from the group consisting of a nonionic surfactant, an ionic surfactant, an amphoteric surfactant, and commercially-available mixtures thereof. An amphoteric surfactant (such as baby-type shampoo) is a surfactant that can function as an anionic surfactant or as a cationic surfactant, depending upon the pH of the medium or system within which the amphoteric surfactant is contained. Moreover, a number of commercially-available emulsifier compositions, some of which are known in the art as "Triton X-100", "Triton X-193" and the like, are illustrative of suitable foam-causing ingredients, for purposes of the present invention.

Additional suitable foam-causing ingredients include synthetic anionic detergents, such as soap systems based upon neutralized carboxylic acids, alkyl aryl sulfonates, alpha-olefin sulfonates, alkyl sulfonates or sulfates, and the like. Also suitable as foam-causing ingredients are nonionic surfactants such as ethoxylated alcohols, alkylphenol ethoxylates, and the like.

One presently preferred nonionic surfactant is an ethoxylated nonyl phenol having about 9 to about 10 moles of ethylene oxide in its chain.

The foam-causing ingredient is primarily utilized as a foam-forming compound. Suitable ingredients for this purpose still further include a commercially-available emulsifying wax (known in the art by its brand name "Polawax"), a sodium salt of a secondary alkane sulfonate (known in the art by its brand name "Hostapur SAS 60"), and a well-known ingredient combination comprising "sorbitan monooleate" as a first ingredient and "POE 20 sorbitan monooleate" as a second ingredient. In the art, these two ingredients are known by their respective brand names "Span 80" and "Tween 80". The weight ratio of Span 80 to Tween 80 ranges from about 1.0:1.5 to about 1.5:1.0, and is preferably 1 to 1; while for other well-known combinations, the preferred weight ratios will of course vary.

Some of these compounds and/or combinations of ingredients, moreover, have some of the aspects of (or function as) emulsifiers.

Suitable foam stabilizers, for purposes of the present invention, include alkanolamides, betaines, cellulosic polymers, and the like.

One such suitable foam stabilizer, presently preferably used in combination with the ethoxylated nonyl phenol (mentioned above) is an alkanolamine. One such suitable, illustrative, commercially-available alkanolamide is known in the art by its brand name, "Witcamide 82".

Still further, and in the alternative, the foam-causing portion of the present invention, for purposes of the present invention, can be characterized as a two-component "foamable system" comprising a saponifiable fatty acid, and an alkali selected from the group consisting of TEA, sodium hydroxide (NaOH), potassium hydroxide (KOH), morpholine (i.e. tetrahydro-1,4-oxazine), and the like. Suitable saponifiable fatty acids include stearic acid, palmitic acid, oleic acid, myristic acid, linoleic acid, and the like. Presently-preferred, suitable saponifiable fatty acids include stearic acid and palmitic acid.

Other suitable foamable systems include, but are not limited to, oleic acid and morpholine, myristic acid or palmitic acid and NaOH or KOH, and the like. A presently preferred foamable system comprises stearic acid, and triethanolamine (TEA).

Suitable insecticidally-active toxidants, in accordance with the present invention, include cypermethrin, other synthetic pyrethroids (such as permethrin, deltamethrin, alphamethrin, and cyphenothrin and the like), natural pyrethrum, organo phosphates, and the like. One such suitable organo phosphate is known in the art by its brand name "Dursban" (i.e. chlorpyrifos).

The presently-preferred insecticidally-active toxidant is selected from the group consisting of cypermethrin, and permethrin.

In addition to the above-identified ingredients, the water-soluble, foamable insecticide composition of the present invention can optionally include a fragrance, a microorganism growth inhibitor or preservative, and/or a metal-corrosion inhibitor. It can be appreciated that inclusion of a preservative and/or a metal-corrosion inhibitor is desirable, for a variety of reasons. The foamable insecticide composition can further optionally include a disinfectant agent, a dye or pigment to produce colored foams, cleaning agents to clean the surface onto which the foam composition is applied, and the like, if desired.

One such illustrative microorganism growth inhibitor or preservative is formaldehyde.

Illustrative of a suitable metal-corrosion inhibitor, for purposes of the present invention, is a compound selected from the group consisting of sodium benzoate, sodium nitrite, and the combination comprising sodium benzoate and sodium nitrite.

Further principles of the present invention can be ascertained from the following examples.

EXAMPLE 1

Water-Soluble Insecticide Composition, Able to Form a Foam That is Stable for 1 Hour

| Ingredient | Function Served | Wt. % |
|---|---|---|
| Ethoxylated nonyl phenol having about 9 to about 10 moles of ethylene oxide in its chain[a] | foaming agent (i.e. functions as an emulsifier, a solublizer and a dispersant) | 2.5 |
| Alkanolamide[b] | foam stabilizer | 0.5 |
| Cypermethrin[c] | insecticidally-active toxidant | 0.2 |
| Fragrance[d] | enhances human acceptance | 0.2 |
| Water | constitutes the major portion of the aqueous phase | 80.9 |
| Formaldehyde[e] | preservative | 0.2 |
| Sodium Benzoate[f] | corrosion inhibitor | 0.5 |

-continued

| Ingredient | Function Served | Wt. % |
|---|---|---|
| A-46[g] | propellant | 15.0 |

[a] A nonionic surfactant.
[b] One such alkanolamide, known in the art as "Witcamide 82" and commercially available from the Witco Chemical Corp., is classified as a viscosity modifier and/or foam stabilizer of the nonionic type, and is reported to be useful as a general thickening agent and as a base for scrub-soap formulations.
[c] Technical grade.
[d] Optional ingredient. A commercially-available lemon fragrance.
[e] Optional ingredient. Prevents the growth of microorganisms.
[f] Optional ingredient. Inhibits metal corrosion.
[g] A-46 is a propellant commercially available from Phillips Petroleum, Bartleville, Oklahoma 74004.

EXAMPLE 2

Water-Soluble Insecticide Compositions, Able to Form a Foam That is Stable for Over 1 Week

| Ingredient | Function Served | Wt. % |
|---|---|---|
| Stearic acid | one of two soap ingredients | 2.66 |
| 85% triethanolamine[h] | the other soap ingredient | 1.58 |
| Cypermethrin | insecticidally-active toxicant | 0.20 |
| Fragrance[i] | to enhance human acceptance | 0.20 |
| Formaldehyde | preservative | 0.20 |
| Water[j] | constitutes the major portion of the aqueous phase | 80.16 |
| A-46 | propellant | 15.00 |

[h] Weight percent, based upon total weight of the "other" soap ingredient (i.e. the second one of the two soap ingredients). The remainder of the "other" soap ingredient is about 15 wt. % (maximum) of diethanolamine and about 0.5 wt. % (maximum) of monoethanolamine.
[i] Same as in EXAMPLE 1.
[j] Deionized water is preferred.

EXAMPLES 1 and 2 correspond to two water-soluble foams having differing levels of foam stability. For example, while the EXAMPLE 1 foam is a relatively wet foam having a stability of about 1 hour, the EXAMPLE 2 foam is much more stable. In particular, the EXAMPLE 2 foam, when formed-in-place in pipes of about 1-inch inner diameter, was observed to remain substantially stable, while retaining its insecticidally-active character for over 1 week.

One method for producing the water-soluble foamable insecticidally-active composition of the present invention comprises combining, in aqueous media, preferably utilizing agitation, (1) an insecticidally-active toxicant together with (2) an effective amount of a foam-causing ingredient capable of dispersing the insecticidally-active toxicant throughout an aqueous phase, for producing an admixture. Such an admixture, when combined with water, is able to produce a foamable, toxicant-in-water dispersion which, in turn, is able to form a water-soluble and insecticidally-active foam. The admixture may further preferably include, as an optional ingredient, a foam stabilizer. The method further comprises adding to the admixture, preferably utilizing agitation, an effective amount of an aqueous phase comprising water, to produce the foamable, toxicant-in-water dispersion. The foamable dispersion is preferably contained in a pressurized container. Next, particles of the foamable dispersion in the pressurized container are preferably released from the pressurized container and carried by the pressurizing agent contained therein, thereby forming the water-soluble and insecticidally-active foam in place. Such foam expands substantially, once formed. Preferably, the water-soluble and insecticidally-active foam is applied into cavities such as cracks and crevices, around and under doorways, and the like.

Other methods of producing the water-soluble, foamable and insecticidally-active composition of the present invention are set forth in EXAMPLES 3 and 4, below.

EXAMPLE 3

Method of Producing the Water-Soluble Foamable Insecticidally-Active Composition of Example 1

The nonionic surfactant, the alkanolamide, and the insecticidally-active toxicant (all listed in EXAMPLE 1), were combined, together with the optional fragrance (also listed in EXAMPLE 1), and were mixed until uniform at room temperature (i.e. about 25° C.). Next, water was added (preferably slowly and with agitation to avoid excessive foaming), thereby producing a uniform, aqueous admixture. (At the beginning of water addition, gelatination may occur; but with further water addition, the viscosity of the admixture can generally be observed to decrease sharply). When the admixture was noted as being substantially uniform, the optional formaldehyde and sodium benzoate ingredients (also listed in Example 1) were added; and the resultant admixture was preferably agitated until these optional ingredients were observed as being substantially dissolved. The subsequent admixture, containing the substantially dissolved optional ingredients, was then placed (together with the propellant) into an aerosol container, and the aerosol container sealed and pressurized.

EXAMPLE 4

Method of Producing the Water-Soluble Foamable Insecticidally-Active Composition of Example 2

The stearic acid (listed in EXAMPLE 2) was heated to a temperature of about 70° to about 75° C. until melted. Separately, the water (also listed in EXAMPLE 2) was heated to a temperature of about 70° to about 75° C. The predominantly TEA-containing ingredient was then added to the heated water, and the resultant TEA-containing aqueous mixture agitated until uniform. Once uniform, and the while the TEA-containing aqueous mixture was still at a temperature of about 70° C. to about 75° C., the melted stearic acid was added, with agitation, thereby producing an admixture. The admixture was thereafter allowed to cool to a temperature of about 70° C. to about 20° C., and the cypermethrin ingredient was added, with agitation. After the cypermethrin-containing admixture was allowed to cool to a temperature of about 40° C. to about 20° C., the optional fragrance and formaldehyde ingredients were added, with agitation. (The subsequent admixture was preferably allowed to cool to prevent losses of perfume and/or formaldehyde.) The subsequent admixture containing the optional ingredients was then placed together with the propellant in an aerosol container, and the aerosol container sealed and pressurized.

What has been described herein is a novel water-soluble, foamable, insecticidally-active composition, and methods for producing the composition. While the foamable composition, including the methods of producing the foamable composition, have been described with reference to preferred embodiments, the invention is not limited thereto. On the contrary, alternatives, changes or modifications will become apparent to those skilled in the art upon reading the foregoing description. Accordingly, such alternatives, changes and modifications are to be considered as forming a part of the invention insofar as they fall within the spirit and scope of the appended claims.

I claim:

1. A water-soluble, foamable, insecticidally-active composition comprising:
    an aqueous phase comprising water;
    an aqueous phase-dispersible and insecticidally-active toxicant; and
    an effective amount of a foam-causing ingredient which is also capable of causing the insecticidally-active toxicant to be dispersed throughout the aqueous phase so as to produce a toxicant-in-water dispersion, for causing the toxicant-in-water dispersion to form a water-soluble and insecticidally-active foam,
wherein the composition is characterized as an insecticidally-active, water-soluble foam wherein the foam-causing ingredient is characterized as a two-component system comprising a saponifiable fatty acid, and an alkali selected from the group consisting of triethanol amine, sodium hydroxide, potassium hydroxide, and morpholine.

2. The water-soluble, foamable, insecticidally-active composition in accordance with claim 1 and further comprising a foam stabilizer.

3. The water-soluble, foamable, insecticidally-active composition in accordance with claim 1 and further comprising an effective amount of a propellant, for causing the foam-causing ingredient-containing toxicant-in-water dispersion to produce a water-soluble and insecticidally-active foam.

4. The water-soluble, foamable, insecticidally-active composition in accordance with claim 3 wherein the propellant is immiscible with the aqueous phase.

5. The water-soluble, foamable, insecticidally-active composition in accordance with claim 1 wherein the foam-causing ingredient is selected from the group consisting of a nonionic surfactant, an ionic surfactant, an amphoteric surfactant, and mixtures thereof.

6. The water-soluble, foamable, insecticidally-active composition in accordance with claim 1 wherein the foam-causing ingredient functions as an emulsifier.

7. The water-soluble, foamable, insecticidally-active composition in accordance with claim 1 wherein the saponifiable fatty acid is selected from the group consisting of stearic acid, palmitic acid, oleic acid, myristic acid, and linoleic acid.

8. The water-soluble, foamable, insecticidally-active composition in accordance with claim 1 wherein the insecticidally-active toxicant is selected from the group consisting of cypermethrin, synthetic pyrethroids, natural pyrethrum, and organo phosphate.

* * * * *